US006006751A

United States Patent [19]
Spitzer

[11] Patent Number: 6,006,751
[45] Date of Patent: Dec. 28, 1999

[54] GLOVE FOR PREVENTING CARPAL TUNNEL SYNDROME

[76] Inventor: A. Robert Spitzer, 4375 Borland Ave., West Bloomfield, Mich. 48323

[21] Appl. No.: 09/121,080

[22] Filed: Jul. 22, 1998

[51] Int. Cl.⁶ ........................................................ A61F 5/37
[52] U.S. Cl. .......................... 128/878; 128/878; 602/20; 602/21
[58] Field of Search .................................. 128/846, 869, 128/877, 878, 879; 602/20, 21; 2/16, 17, 18, 19, 159–162

[56] References Cited

U.S. PATENT DOCUMENTS

| | | | |
|---|---|---|---|
| 4,709,694 | 12/1987 | O'Connell | 602/21 |
| 5,031,640 | 7/1991 | Spitzer . | |
| 5,454,380 | 10/1995 | Gates | 128/845 |
| 5,766,141 | 6/1998 | Gould | 602/21 |
| 5,810,753 | 9/1998 | Eberbach | 602/20 |

*Primary Examiner*—Michael A. Brown
*Attorney, Agent, or Firm*—Kohn & Associates

[57] ABSTRACT

A glove assembly (20) adapted to inhibit or prevent carpal tunnel syndrome includes a flexible glove body (22) having a front side (24) and a back side (26) which defines a wrist opening (28) and at least one finger opening (30). The glove assembly (20) further includes a resilient protector (32), secured to the front side (24) of the glove body (22), for preventing the application of pressure to a median nerve. The resilient protector (32) defines a recess (36) extending substantially parallel with both sides (38) of the median nerve. It is also interrupted along its extent thereby imparting greater flexibility and ease of movement to a wearer of the glove assembly (20). A grip is also disclosed which includes a resilient protector interrupted along its extent.

20 Claims, 5 Drawing Sheets

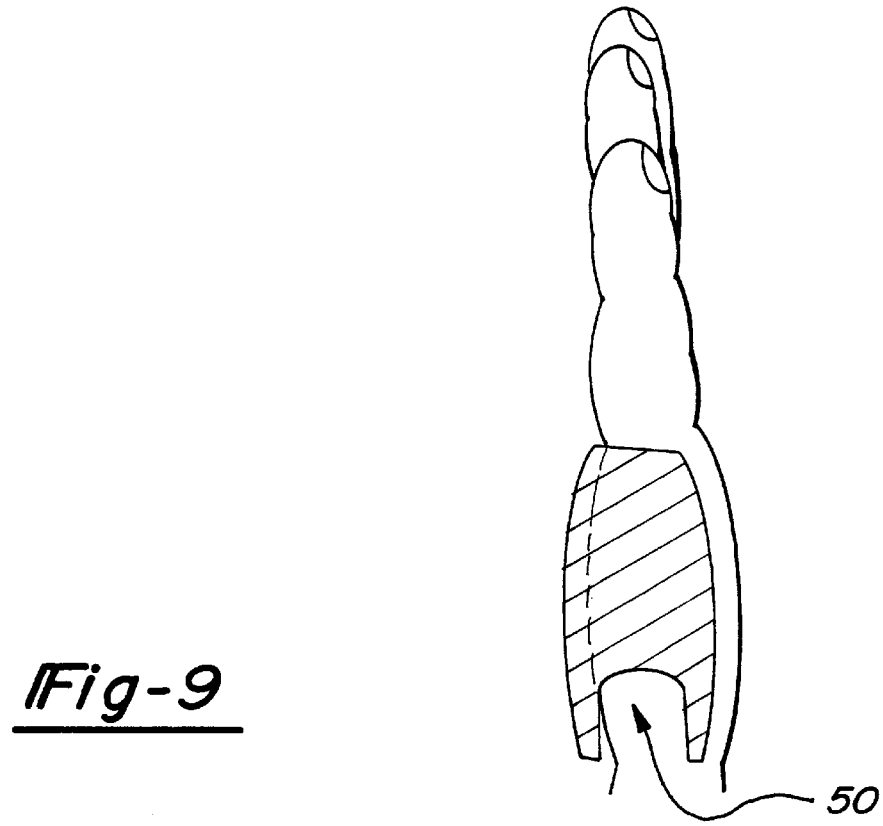
*Fig-9*
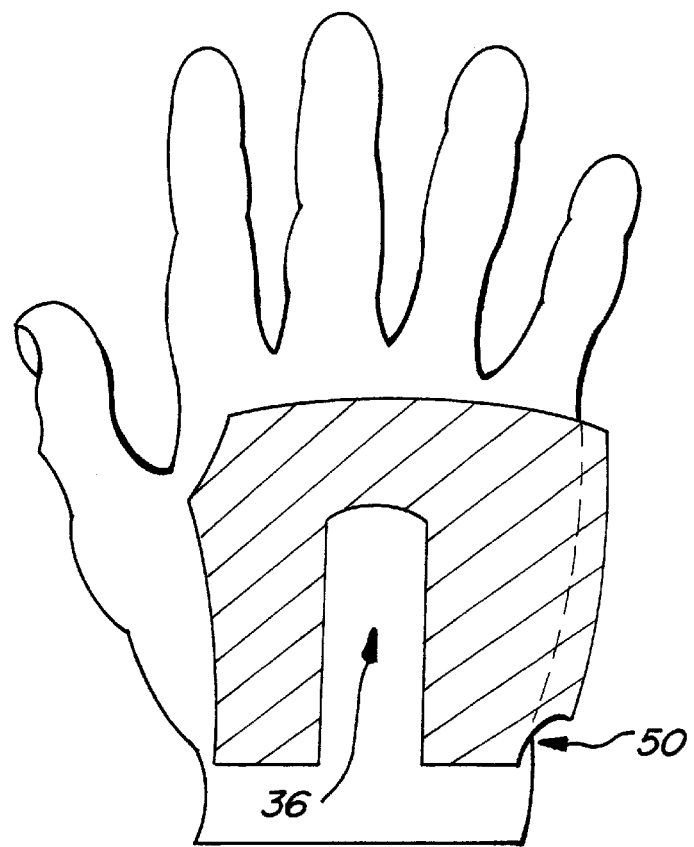

GLOVE FOR PREVENTING CARPAL TUNNEL SYNDROME

BACKGROUND OF THE INVENTION

1. Field of the Invention

The invention relates to a glove which is adapted to inhibit or prevent carpal tunnel syndrome. Particularly, the present invention relates to a glove assembly which inhibits or prevents carpal tunnel syndrome while providing increased flexibility and ease of movement to the wearer of the glove assembly.

2. Description of Related Art

Carpal tunnel syndrome is a common condition which occurs due to the compression of the median nerve. It is sometimes referred to as median compression neuropathy within the carpal canal. Carpal tunnel syndrome is a particular problem for workers in industries which require manual operations with hand held implements or tools or in office situations wherein a worker may be required to spend several hours a day resting their hands on a typewriter or computer terminal and may also be sports related.

Carpal tunnel syndrome is a clinical syndrome characterized by numbness, weakness, paraesthesia or atrophy in the territory of the median nerve distal to the course through the carpal tunnel in the wrist. The transverse carpal ligament forms over the median nerve and may compress the median nerve as a result of pressure on the hand, producing the above described symptoms. Traumatic injury is exacerbated because of the narrowness of the carpal canal. There is no opportunity for the nerve to be displaced away from any compressive forces. Compressive injury can be exacerbated by the development of edema in the tissues within the canal, which because of the relatively fixed size, can cause added injury due to compression of the nerve within the canal. An additional component of the injury is associated with friction between the nerve and the adjacent tendons caused by repetitive motions (injury) which may be worsened by compression and further reduce the available space within the canal.

Two types of injury can occur due to compression of the median nerve. The milder, earlier form is a demyelination of the median nerve within the canal. This type of demyelination occurs early in the course of compressive injury. However, this form of injury is also more readily reversible and recovery can occur in four to six weeks after compression is relieved. This form of injury can cause motor weakness due to acute conduction block in the nerve, however, this weakness is readily reversible.

The second major form of injury includes damage to the axons themselves. This form of injury occurs in more severe or prolonged cases and has more significant implications in that it often leads to motor weakness. This type of motor weakness tends to be poorly reversible and often irreversible. Loss of strength in the thenar muscles can lead to major disabilities due to the loss of ability to grip or perform fine dexterous manipulations. This second form of injury is generally seen in long-standing cases, many of which, first clinically manifest in a manner suggestive of the demyelinating form.

If the median nerve is injured at the wrist, as by wounds or by a dislocation of the lunate bone, sensation may be lost in the skin on the front of the index finger and adjacent part of the thumb and over the back of the distal phalanges of the thumb, index finger, and middle fingers, and is diminished over a large area. The brunt of the paralysis falls on the muscles of the thenar eminence which, in time, flattens and wastes.

Treatment of carpal tunnel syndrome varies according to the severity of the condition. Severe conditions usually require hand surgery to sever the transverse carpal ligament, whereas in less severe cases, a splint may be utilized to immobilize the wrist.

In order to prevent or inhibit a person from development carpal tunnel syndrome, a number of gloves and wrist braces have been designed. One such glove is disclosed in U.S. Pat. No. 4,850,341 to Fabry et al., issued Jul. 25, 1989, which discloses a glove for inhibiting or preventing carpal tunnel syndrome which includes a pad configured to cover and protect the median nerve of the wearer's hand. The problem with such a device is that the pad is placed directly over the median nerve and, therefore, transmits pressure from the external source to the carpal tunnel ligament. With this type of relationship, repetitive finger movements can increase the potential for frictional injury. Additionally, having a pad oriented directly over the median nerve, allows for the direct transmission of pressure to the median nerve.

In order to overcome the problems associated with the type of glove disclosed in the Fabry et al. patent, a pad design was disclosed in U.S. Pat. No. 5,031,640 to applicant, issued Jul. 16, 1991 and incorporated herein by reference, which eliminates the continuous pressure applied directly over the median nerve by providing a recess over the median nerve in a support pad thereby preventing or eliminating carpal tunnel syndrome. This type of design has proven to be very effective in inhibiting or preventing carpal tunnel syndrome. However, it would be advantageous and desirable to incorporate into the pad which eliminated continuous pressure directly over the median nerve, a means of improving the flexibility and ease of movement to the wearer of the glove containing such a pad.

SUMMARY OF THE INVENTION

According to the present invention, there is provided an assembly adapted to inhibit or prevent carpal tunnel syndrome including a body having a front side. The assembly includes resilient protection means secured to the front side of the body for preventing the application of pressure to a median nerve. The resilient protection means includes parallel portions defining a recess extending therebetween and substantially parallel with both sides of the median nerve when disposed thereon. The resilient protection means is interrupted along the extent thereof thereby imparting greater flexibility and ease of movement to a user relative to the assembly.

DESCRIPTION OF THE DRAWINGS

Other advantages of the present invention will be readily appreciated as the same becomes better understood by reference to the following detailed description when considered in connection with the accompanying drawings wherein:

FIG. 9 is a plan view of another embodiment of the present invention disposed on a hand.

DETAILED DESCRIPTION OF THE INVENTION

A glove assembly adapted to inhibit or prevent carpal tunnel syndrome for use on a hand 10 is generally shown at 20 in the Figures. The hand 10 is shown broken away to show the median nerve 34 and adjoining tissue.

It should be noted that although the assembly is shown as a glove 20, the invention can take the form of a grip, such as a grip on a bicycle handle bar or a work tool.

Figure 1:
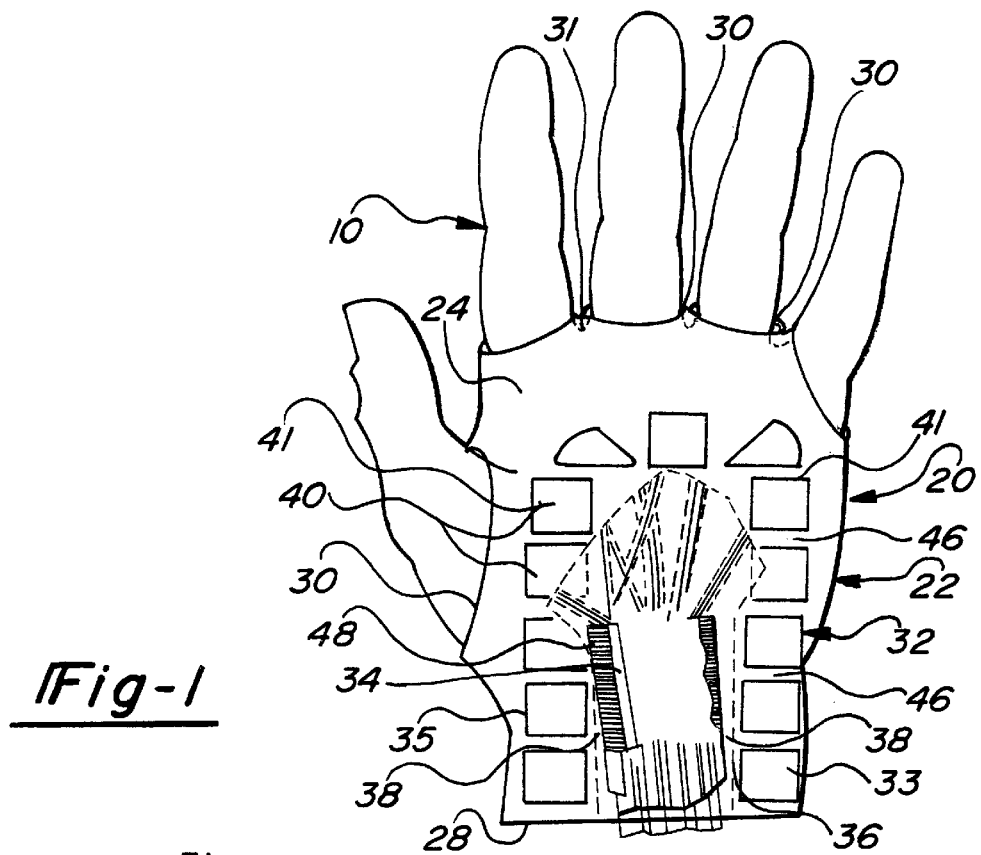
FIG. 1 is a particularly cut-away view of an embodiment of the subject invention.

Referring to FIG. 1, the assembly 20 includes a flexible glove body generally indicated at 22. The glove body includes a front side 24 and a back side 26 defining a wrist opening 28 and at least one finger opening 30. A resilient protection pad or cushion mechanism, generally indicated at 32, is secured to the front side 24 of the glove body 22 for preventing the application of pressure to a median nerve 34 located in the hand 10. The resilient protection pad or cushion mechanism 32 includes two parallel portions 33, 35 which define a recess 36 therebetween. The recess extends substantially parallel with both sides 38 of the median nerve 34 when the glove 20 is worn.

The resilient protection pad or cushion mechanism 32 includes interruptions 46 which impart greater flexibility and ease of movement to a wearer of the glove assembly 20. That is, the pad mechanism 32 is not a flat surfaced cushion, but rather, a cushion presenting an interrupted surface including flexible portions at the interruptions. The interruptions provide points or areas of greater flexibility allowing for greater flexibility of the glove at the grip thereof as well as the need for less padding material. Hence, greater functionability at a lower cost is achieved.

By way of background, the hand 10 and median nerve 34 are illustrated in detail in FIG. 1. The median nerve 34 flattens out under the flexor retinaculum 48 and deep to the superficial palmar arch and palmar aponeurosis, lying on the flexor tendons, and divides into five terminal palmar digital branches and a muscular branch. The tendons and median nerve 34 are packed within and extend under the flexor retinaculum 48.

The pad or cushion mechanism of the glove assembly 20 distributes pressure away from the median nerve 34 and onto the adjacent soft tissue structures, such as muscle, bone and/or fat. The region of the pad located over the median nerve 34 has no material disposed thereover, or may contain a material sufficiently softer or thinner than the surrounding material. By eliminating pressure directly over the median nerve 34, the pressure is also eliminated from the area directly surrounding the median nerve 34 which thereby allows the tendons and median nerve 34 to move without frictional or direct pressure injury to the median nerve 34. The greater flexibility of the pad or cushion mechanism 32 of the present invention adds to the effectiveness of the redistribution effect while allowing freer movement to grip.

Referring more specifically to the glove assembly 20, the front side 24 and back side 26 of the flexible glove body 22 are typically sewn together in a face-to-face relationship to define the glove body 22 or otherwise formed by methods known in the art. The material comprising the glove body 22 can include a separate glove front 24 and back 26 which are sewn together in the face-to-face relationship to define the glove body 22 or can be formed of a single piece of material which is sewn together in a sock-like fashion to define the glove body 22 having the wrist opening 28 and at least one finger opening 30.

Figure 2:
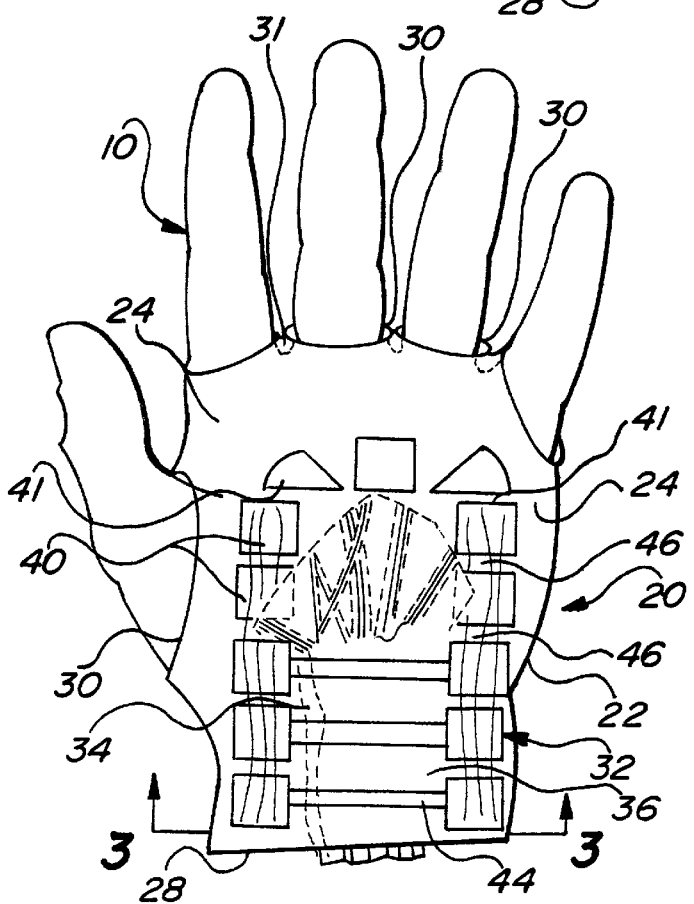
FIG. 2 is a partially cut-away view of a second embodiment of the subject invention.
Figure 4:
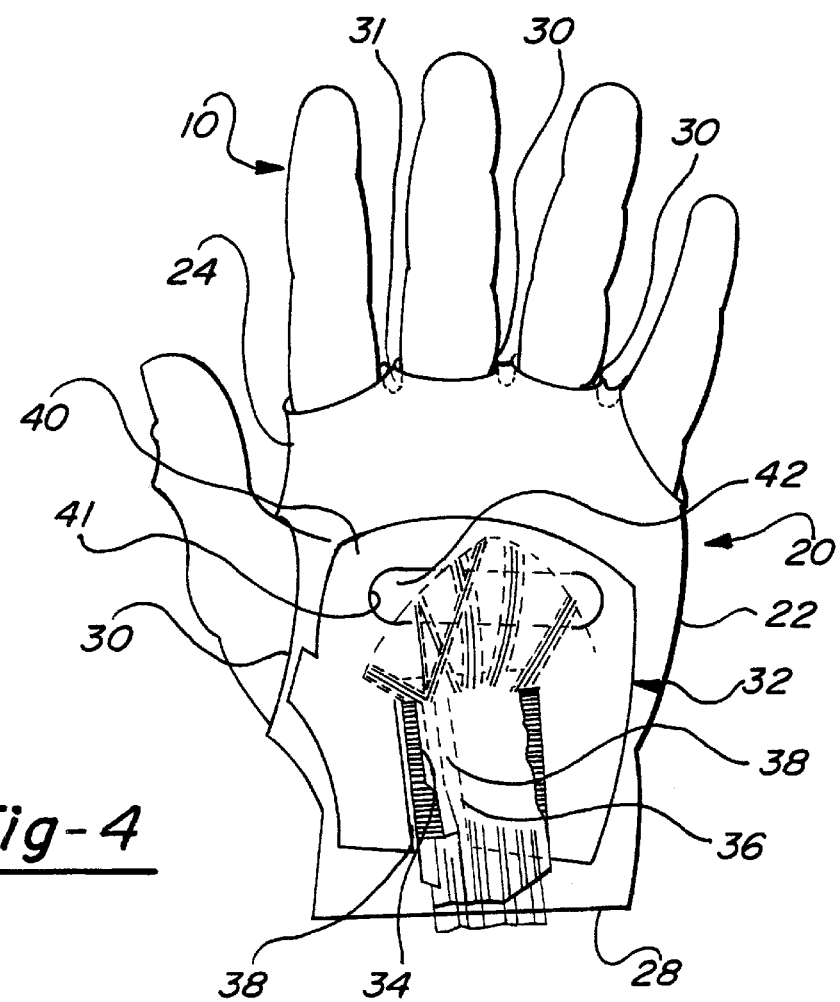
FIG. 4 is a partially cut-away view of a third embodiment of the subject invention.

The finger opening 30 can be partitioned or subdivided into separate finger openings by the addition of partitions 31 which can include a line of stitching between the front side 24 and back side 26 of the glove body thereby defining separate finger openings 30 or can include the addition of a loop of material which is attached to the front side 24 and back side 26 to define the finger opening 30. Additionally, a thumb opening can be included as a finger opening 30 as shown in FIGS. 1, 2, and 4. Again, various glove constructions can be used and made by those skilled in the art.

The flexible glove body 22 can also include a fastener or closure (not shown) located near the wrist opening 28 to secure the glove assembly 20 to the wrist portion of the hand 10 as a wrist splint. The closure can include an elastic band (not shown) sewn into the flexible glove body 22 directly adjacent to the wrist opening 28 or can include a VELCRO-type male/female closure as is well known to those skilled in the art. Alternatively, the glove can be a slip-on glove or other style known in the art, although it is preferable to have a fit which maintains the pads or cushion mechanism oriented appropriately relative to the palm of the hand and especially relative to the median nerve.

Generally, the glove body 22 is constructed of a flexible or expandable elastic-type material which conforms to the hand 10 of the user. The flexible material provides a more secure fit for the glove assembly 20 and provides a "good feel" to the wearer of the glove assembly 20. The material which comprises the glove body 22 can be a flexible material such as SPANDEX or other similar fabric which imparts elasticity to the glove assembly 20. However, the glove body 22 of the glove assembly 20 can be made of any suitable natural material such as cotton, wool, and leather, synthetic materials such as nylons (Kevlar™ of Dupont) and polyesters, or any combination thereof.

As best illustrated in FIGS. 1, 2, and 4, the resilient protection pad or cushion mechanism 32 is secured to the front side 24, better known as the palm side, of the glove body 22. The resilient protection pad or cushion mechanism 32 can be made up of several individual cushions or pads 40 which are secured or affixed to the front side 24 of the glove body 22. The pads 40 can be secured by any suitable means such as sewing, gluing, molding in place or other similar affixing method. The pads 40 can take on various forms, as discussed below.

The mechanism also can be a single horseshoe shaped pad having recessed portions in the surface thereof. The recessed portions can provide the flex areas between the relatively raised portions.

The resilient protection pad or cushion 32 can include at least one pad or cushion 40 disposed on the front side 24 of the glove body 22. The orientation of the pad or pads which makes up the resilient protection pad or cushion 32 defines the major recess 36 which extends substantially parallel with both sides 38 of the median nerve 34. The recess 36 is within a predetermined size range for eliminating pressure directly over and in the vicinity of the median nerve 34. The recess 36 is placed directly over the median nerve 24 and extends to cover the surrounding soft tissues adjacent to the median nerve 36. That is, the median nerve 34 lies safely under the recess 36 defined by inner margins 41 of the pad or pads 40.

The median nerve 34 is approximately three millimeters wide between the base of the thumb and opposite side of the wrist and should have protection between the crease of the wrist and the first creases of the palm. Accordingly, the recess 36 must be of greater size than the median nerve 34. Additionally, the recess 36 should be designed to allow for some error in positioning the recess 36 of the resilient protection pad or cushion 32 over the median nerve 34. The depth of the recess 36 and the resiliency and hardness of the cushion pad 40 must be such that when pressure is placed on the hand 10 to cause depression of the pad 40, the median nerve 34 will not have undue pressure against the external object placing pressure on the hand 10. In this manner, the median nerve 34 is supported away from the surface of the external object.

The pad or pads 40 which make up the resilient protection pad or cushion mechanism 32 are arranged in such a pattern that interruptions or non-protected void spaces are established between adjacent pads 40. These interruptions or void spaces 46 allow the wearer of the glove assembly 20 to have greater flexibility and ease of movement of the hand 10 within the glove in order to perform manual operations such as typing or grasping of a tool.

The interruptions or void spaces 46 are preferably small enough to allow for the increased flexibility and ease of movement of the hand 10 of the wearer while, at the same time, preventing the infiltration or penetration of external objects into the interruptions or void spaces 46.

The interruptions 46 can also be in the form of alternating or differentially oriented segments of softer and harder materials which comprise the resilient protection pad or cushion 32. The resilient protection pad or cushion 32 can be comprised of materials which have alternating segments of materials which have different flexibilities or firmness in order to improve the movement of the wearer of the glove assembly 20.

Referring to FIG. 4, an alternative embodiment of the present invention is shown wherein the glove assembly 20 includes a cushion pad 40 having an internal portion 42 removed to improve the flexibility of the cushion pad 40. The pad 40 includes an interruption or void portion 42 which imparts greater flexibility to the wearer of the glove 20. This embodiment demonstrates that the interruption 42 in the resilient protection cushion or pad 32 can take many different forms thereby providing increased flexibility and ease of movement to the wearer of the glove assembly 20 and without departing from the spirit of the invention.

Figure 7:
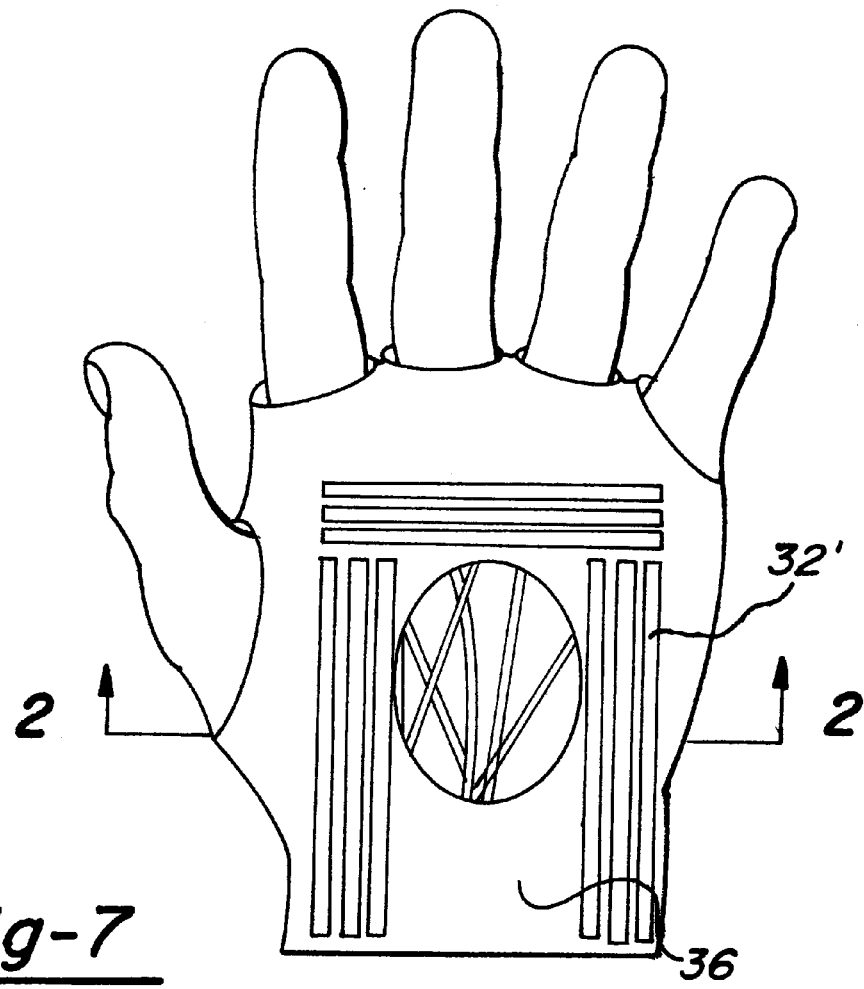
FIG. 7 is a plan view of a further embodiment of the present invention disposed on a hand.
Figure 8:
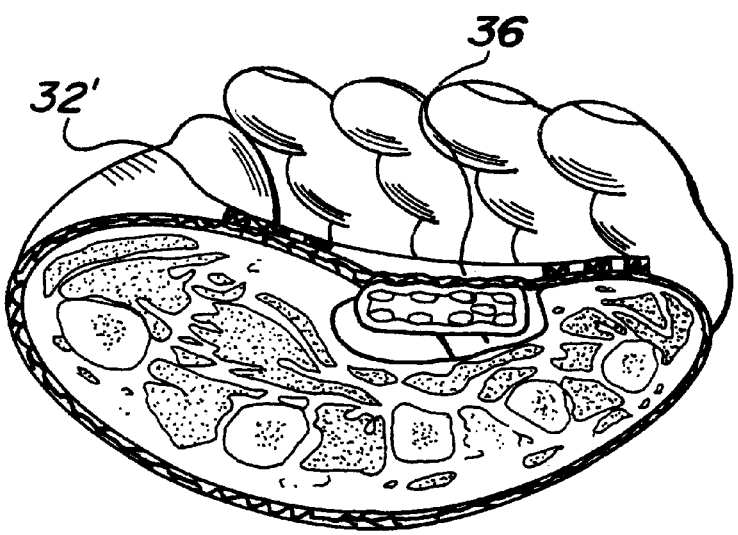
FIG. 8 is a cross-sectional view taken along lines 8—8 of FIG. 7.

FIGS. 7 and 8 show a further embodiment of the present invention wherein strips of cushioning material define the pad mechanism 32'. The strips 32' can be applied by means known in the art for printing or extruding a plastic material onto a glove surface. The strip or segmented design combines flexibility of the glove with ease of manufacturing. It also allows for a wide selection of designs that provide a recess 36.

The resilient protection pad or cushion mechanism 32 which is comprised of the pad or pads 40 must have sufficient firmness to protect the palm of the hand overlying the median nerve 34 from shock, pressure, and vibration, but should have sufficient flexibility to permit the wearer to effectively grasp and use a tool or perform manually dexterous operations while wearing the glove 20. The protective pad or cushion 32 which is comprised of the pad or pads 40 is preferably constructed of an elastomeric material, such as foam rubber or other materials such as closed-cell neoprene, ethylene propylene terpolymer, styrene butadiene, urethane polymer, and other similar elastomers.

Any of the materials used to construct the resilient protection pad or cushion 32 can be formed first then secured to the front side 24 of the glove body 22 by means such as gluing or sewing, or the materials such as polyurethane can be molded, injected, or foamed-in-place on the front side 24 of the glove body 22. Molding or injecting operations such as foaming-in-place allow for the introduction of air bubbles, void spaces, or closed cells within the material comprising the protection pad or cushion 32 thereby imparting greater pressure, vibration, and shock dampening capacity to the protection pad or cushion 32.

In an additional embodiment illustrated in FIGS. 2, 3, 5, and 6, a bridge 44 is shown which extends across the recess 36 and is affixed to the resilient protection pad or cushion 32 for preventing external objects from penetrating the recess 36 and thereby contacting the median nerve 34 or surrounding tissue. Also, contact of the bridge by the object being gripped directs forces from the recess area, through the bridge laterally to the pads. Thus, forces are further transferred from the area over the median recess laterally away therefrom.

Figure 3:
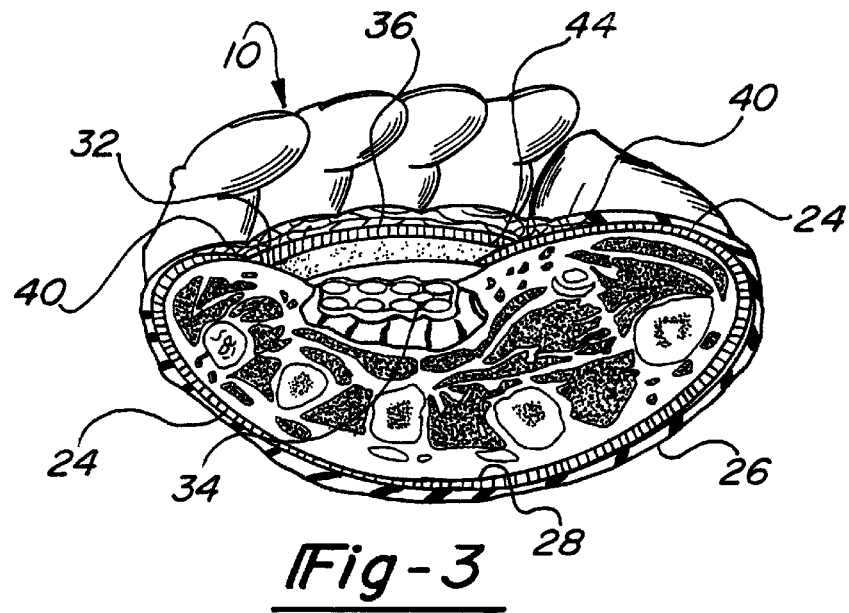
FIG. 3 is a partially cut-away view taken along lines 3—3 of FIG. 2.

Generally, the bridge 44 is constructed of a material which is less resilient than the material which comprises the resilient protection cushion or pad 32. The bridge 44 can take any suitable shape necessary to prevent the penetration or infiltration of external objects into the recess but preferably can be "domed" shaped, as best shown in FIG. 3, and extends away from the surface of the resilient protection pad or cushion 32. The glove assembly 20 can include at least one bridge 44 but may include a number of the bridges 44 in order to provide adequate coverage of the recess 36 and protection of the median nerve 34 with use of less material.

Figure 5:
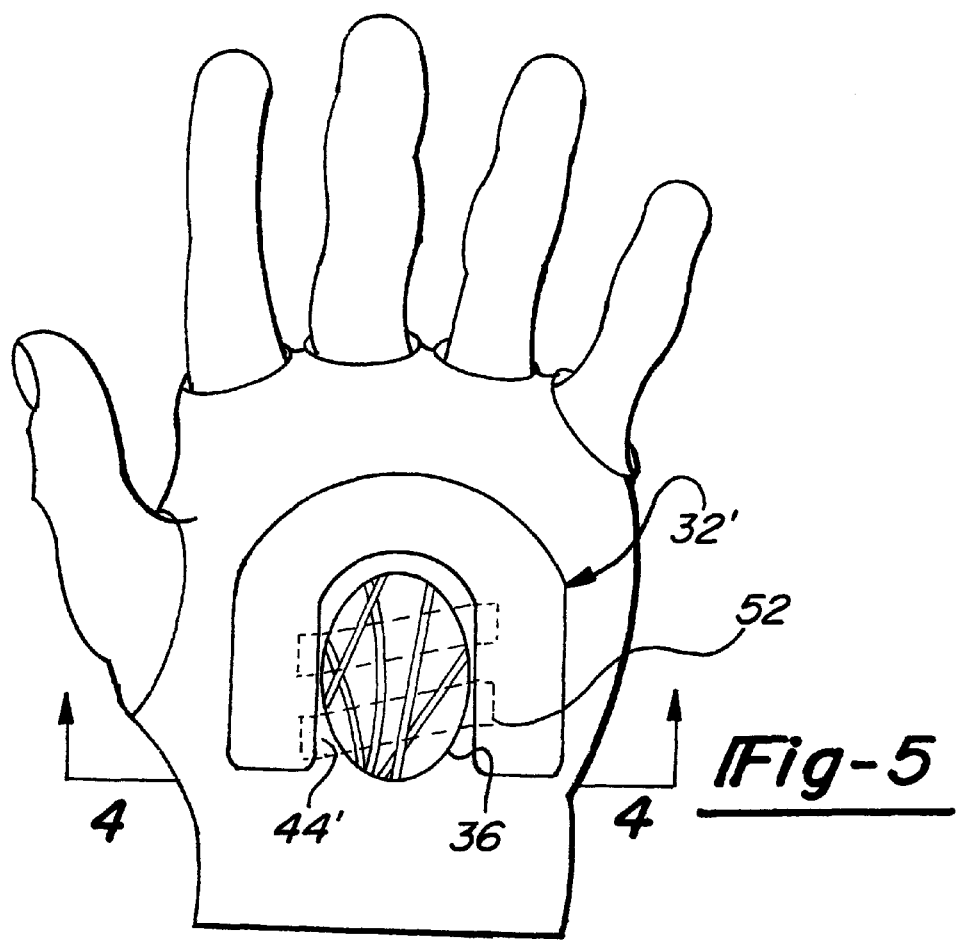
FIG. 5 is a plan view of another embodiment of the present invention disposed on a hand.

For example, FIGS. 2 and 5 show different constructions of the bridge 44'. In FIG. 2, a multi-strip bridge interconnects parallel pads. In FIG. 5, a single unitary horseshoe shape pad includes parallel portions interconnected by wide bridge strips 44'.

Figure 6:
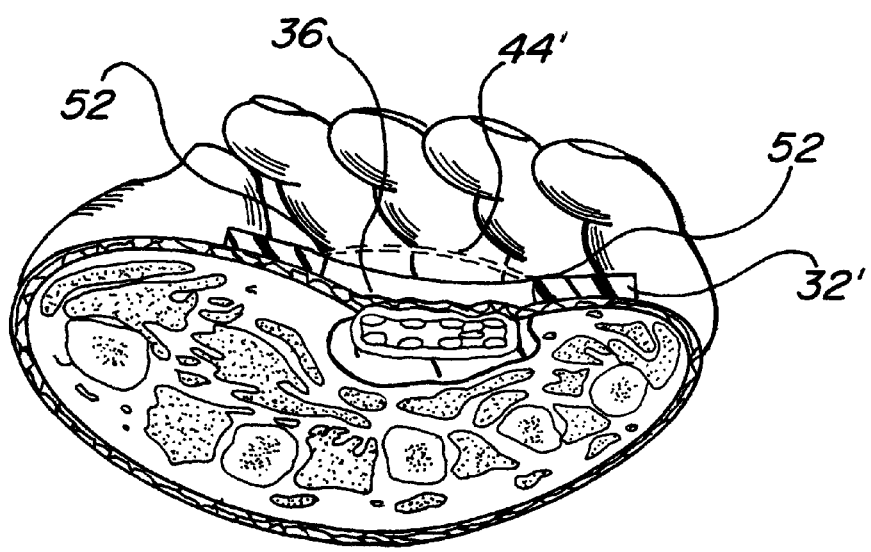
FIG. 6 is a cross-section taken along lines 6—6 of FIG. 5.

In FIGS. 5 and 6, the bridge 44' is connected to the pad 32' by an elastic portion 52. The elastic part 52 allows for more flexibility when utilizing the more rigid bridge 44' in combination with the glove. The elastic portion also further dissipates loads laterally away from the recess 36.

The bridge 44 can be constructed of any suitable material including plastic materials such as polystyrene, polyvinyl chloride, and polyurethane, as well as metals, utilizing methods well known to those skilled in the art of plastic injection, molding, and forming.

Referring to FIG. 9, an alternative embodiment of the resent invention is shown wherein the glove assembly 20 includes a secondary notch 50 which is situated over the ulnar nerve. This notch prevents the compression of the ulnar nerve as well as the median nerve.

Again, each of the species discussed above can be disposed onto a gripping surface, such as a work tool grip or machine grip commonly used in the manufacturing industry. Thus, instead of the user wearing a glove including the pad mechanism of the present invention, the same pad mechanism is disposed on the machine grip and is then appropriately gripped by the user. The issue here is not flexibility, since the grip is usually a solid bar, but rather one of efficient use of materials and bridging over the median nerve.

The invention has been described in an illustrative manner, and it is to be understood the terminology used is intended to be in the nature of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A glove assembly (20) adapted to inhibit or prevent carpal tunnel syndrome, said glove assembly (20) comprising:

a flexible glove body (22) including a front side (24) and a back side (26); and resilient protection means (32) for preventing the application of pressure to a median nerve (34) secured to said front side (24) of said glove body (22), said resilient protection means (32) including parallel portions (33,35) defining a recess (36) therebetween, the recess being substantially parallel with both sides (38) of the median nerve (34), said resilient protection means (32) being interrupted thereby imparting greater flexibility and ease of movement to a wearer of said glove assembly (20).

2. A glove assembly (20) as set forth in claim 1, wherein said resilient protection means (32) includes at least one cushion pad (40).

3. A glove assembly (20) as set forth in claim 2, wherein said resilient protection means (32) includes a plurality of spaced apart cushion pads (40).

4. A glove assembly (20) as set forth in claim 3, wherein said plurality of spaced apart cushion pads (40) are sequentially disposed.

5. A glove assembly (20) as set forth in claim 2, wherein said resilient protection means (32) includes a cushion pad (40) having an internal portion (42) removed to improve the flexibility of said cushion pad (40).

6. A method according to claim 1, wherein said resilient protective means comprises a plurality of groups parallel to strips, said groups forming two parallel lines defining said recess 36 therebetween.

7. A glove assembly (20) as set forth in claim 1, wherein said resilient protection means (32) is constructed of a elastomeric material.

8. A glove assembly (20) as set forth in claim 7, wherein said elastomeric material includes neoprene, ethylene propylene terpolymer, and styrene butadiene.

9. A glove assembly (20) as set forth in claim 1, wherein said resilient protection means (32) is constructed of a plastic material including polystyrene, polyvinyl chloride, urethane, and polyurethane.

10. A glove assembly (20) as set forth in claim 1 further including at least one bridging means (44) disposed between said resilient protection means (32) and over said recess (36) to prevent contact between the median nerve (34) and an external object.

11. A glove assembly (20) as set forth in claim 10, wherein said bridging means (44) is affixed to said resilient protection means (32).

12. A glove assembly (20) as set forth in claim 10, including elastic means interconnecting said bridge means (44) to said resilient protection means (32).

13. A glove assembly (20) as set forth in claim 10, wherein said bridging means (44) is made of a material which is less resilient than the material comprising said resilient protection means (32).

14. A glove assembly (20) as set forth in claim 10, wherein said bridging means (44) is constructed of a plastic material including polystyrene, polyvinyl chloride, and polyurethane.

15. A glove assembly (20) as set forth in claim 14, wherein said bridging means (44) is made of a material which less resilient than material comprising the resilient protection means (32).

16. A glove assembly (20) as set forth in claim 14, wherein said bridging means (44) is constructed of a plastic material including polystyrene, polyvinyl chloride, and polyurethane.

17. A glove assembly (20) adapted to inhibit or prevent carpal tunnel syndrome, said glove assembly (20) comprising:

a flexible glove body (22) including a front side (24) and a back side (26) defining a wrist opening (28) and at least one finger opening (30); and resilient protection means (32) for preventing the application of pressure to a median nerve (34) secured to said front side (24) of said glove body (22), for preventing the application of pressure to a median nerve (34), said resilient protection means (32) defining a recess (36) extending perpendicularly and adjacent to both sides (38) of the median nerve (34); and at least one bridging means (44) disposed between said resilient protection means (32) and over said recess (36) to prevent contact between the median nerve (34) and an external object.

18. A glove assembly (20) as set forth in claim 17, wherein said bridging means (44) is affixed to said resilient protection means (32).

19. A glove assembly (20) as set forth in claim 17 including elastic means interconnecting said bridge means (44) to said resilient protection means (32).

20. An assembly (20) adapted to inhibit or prevent carpal tunnel syndrome, said assembly (20) comprising:

a body (22) including a front side (24); and resilient protection means (32) for preventing the application of pressure to a median nerve (34) secured to said front side (24) of said body (22), said resilient protection means (32) including parallel portions (33, 35) defining a recess (36) therebetween, the recess being substantially parallel with both sides (38) of the median nerve (34) when positioned thereon, said resilient protection means (32) being interrupted.

* * * * *